United States Patent [19]
Berg

[11] Patent Number: 5,904,815
[45] Date of Patent: May 18, 1999

[54] SEPARATION OF T-AMYL ALCOHOL FROM N-BUTANOL BY AZEOTROPIC DISTILLATION

[76] Inventor: Lloyd Berg, 1314 S. 3rd Ave., Bozeman, Mont. 59715

[21] Appl. No.: 09/035,380

[22] Filed: Mar. 5, 1998

[51] Int. Cl.$^6$ .............................. B01D 3/36; C07C 29/82
[52] U.S. Cl. .............................. 203/57; 203/59; 203/60; 203/62; 203/63; 203/58; 203/68; 203/70; 568/913
[58] Field of Search .................................. 203/57, 59, 63, 203/70, 68, 62, 60, 58; 568/913

[56] References Cited

U.S. PATENT DOCUMENTS

| | | | |
|---|---|---|---|
| 4,349,416 | 9/1982 | Brandt et al. | 203/64 |
| 4,693,788 | 9/1987 | Berg et al. | 203/57 |
| 4,756,803 | 7/1988 | Berg | 203/60 |
| 4,874,474 | 10/1989 | Rescalli et al. | 568/913 |
| 4,935,103 | 6/1990 | Berg et al. | 203/64 |
| 5,338,410 | 8/1994 | Berg | 203/58 |
| 5,360,520 | 11/1994 | Berg | 568/913 |
| 5,759,359 | 6/1998 | Berg | 203/57 |

*Primary Examiner*—Virginia Manoharan

[57] ABSTRACT t-Amyl alcohol cannot be separated from n-butanol by distillation or rectification because of the closeness of their boiling points. t-Amyl alcohol is readily separated from n-butanol by azeotropic distillation. Effective agents are propyl acetate, tetrahydrofuran and heptane.

1 Claim, No Drawings

SEPARATION OF T-AMYL ALCOHOL FROM N-BUTANOL BY AZEOTROPIC DISTILLATION

FIELD OF THE INVENTION

This invention relates to a method of separating t-amyl alcohol from n-butanol by azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 | t-Amyl alcohol and n-butanol boil sixteen degrees apart and have a relative volatility of 1.25 which makes it difficult to separate them by conventional distillation or rectification. Table 2 shows that with an agent giving a relative volatilty of 1.5, only 30 actual plates are required to get 99% purity compared to 55 plates for straight rectification.

TABLE 2

Theoretical and Actual Plates Required vs. Relative Volatility for t-Amyl Alcohol From n-Butanol Separation

| Relative Volatility | Theoretical Plates Required At Total Reflux, 99% Purity | Actual Plates Required, 75% Efficiency |
|---|---|---|
| 1.25 | 41 | 55 |
| 1.4 | 26 | 35 |
| 1.5 | 22 | 30 |

OBJECTIVE OF THE INVENTION

The object of this invention is to provide a process or method of azeotropic distillation that will enhance the relative volatility of t-amyl alcohol and n-butanol in their separation in a rectification column. It is a further object of this invention to identify effective azeotropic distillation agents that are stable and can be recycled.

SUMMARY OF THE INVENTION

The objects of this invention are provided by a process for the separation of t-amyl alcohol from n-butanol which entails the use of certain organic compounds when employed as the agent in azeotropic distillation.

DETAILED DESCRIPTION OF THE INVENTION

I have discovered that certain organic compounds will effectively increase the relative volatility between t-amyl alcohol and n-butanol during rectification when employed as the agent in azeotropic distillation. They are triethyl amine, ethylene glycol dimethyl ether, diisobutylamine, acetal, 2,2-dimethyl-butane, 2,3-dimethylbutane, cyclopentane, hexane, 2,2-dimethoxy-propane, butyraldehydr, acetonitrile, sulfolane, propyl acetate tetrahydrofuran, isopropyl ether and heptane.

THE USEFULNESS OF THE INVENTION

The usefulness of this invention can be demonstrated by referring to the data presented in Tables 1, 2 and 3. All of the successful agents show that t-amyl alcohol can be separated from n-butanol by means of azeotropic distillation in a rectification column and that the ease of separation as measured by relative volatility is considerable.

WORKING EXAMPLE 1. nifty grains of t-amyl alcohol—n-butanol mixture and fifty grams of heptane were charged to a vapor-liquid equiibrium still and refluxed for two hours. The vapor composition was 27.5% t-amyl alcohol and 72.5% n-butanol. The liquid composition was 20.2% t,amyl alcohol and 79.8% n-butanol. This is a relative volatility of 1.5.

TABLE 3

Effective Azeotropic Distillation Agents For Separating t-Amyl Alcohol From n-Butanol

| Compounds | Relative Volatility |
|---|---|
| None | 1.25 |
| Triethyl amine | 1.55 |
| Ethylene glycol dimethyl ether | 1.35 |
| Diisobutylamine | 1.35 |
| Acetal | 1.45 |
| 2,2-Dimethylbutane | 1.45 |
| 2,3-Dimethylbutane | 1.45 |
| Cyclopentane | 1.45 |
| Hexane | 1.35 |
| 2,2-Dimethoxypropane | 1.35 |
| Butyraldehyde | 1.4 |
| Acetonitrile | 145 |
| Sulfolane | 1.4 |
| Propyl acetate | 1.45 |
| Tetrahydrofuran | 1.65 |
| Isopropyl ether | 1.4 |
| Heptane | 1.5 |

I claim:

1. A method For recovering t-amyl alcohol from a mixture of t-amyl alcohol and n-butanol which comprises distilling a mixture consisting of t-amyl alcohol and n-butanol in the presence of an azeotrope forming agent, recovering the t-amyl alcohol and the azeotrope forming agent as overhead product and obtaining the n-butanol as bottoms product, wherein said azeotrope forming agent consists of one material selected from the group consisting of triethyl amine, ethylene glycol dimethyl ether, diisobutylamine, 2,2-dimethylbutane, hexane, 2,3-dimethylbutane, cyclopentane, 2,2-dimethoxypropane, butyraldehyde, acetonitrile, sulfolane, propyl acetate, tetrahydrofuran, isopropyl ether and heptane.

* * * * *